United States Patent
Podányi et al.

(10) Patent No.: US 12,054,513 B2
(45) Date of Patent: *Aug. 6, 2024

(54) AMORPHOUS MIXTURE COMPRISING A NEUTRAL MONO- OR OLIGOSACCHARIDE AND AN ACIDIC NON-CARBOHYDRATE COMPONENT

(71) Applicant: GLYCOM A/S, Hørsholm (DK)

(72) Inventors: Benjámin Podányi, Dunakeszi (HU); Pierre Chassagne, Beaumont (FR); Martin Matwiejuk, Hamburg (DE); Markus Jondelius Hederos, Trelleborg (SE)

(73) Assignee: GLYCOM A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,360

(22) Filed: Nov. 21, 2022

(65) Prior Publication Data

US 2023/0102772 A1   Mar. 30, 2023

Related U.S. Application Data

(62) Division of application No. 16/630,372, filed as application No. PCT/IB2018/055136 on Jul. 12, 2018, now Pat. No. 11,505,567.

(30) Foreign Application Priority Data

Jul. 12, 2017 (DK) .......................... PA 2017 70567

(51) Int. Cl.
| | | |
|---|---|---|
| C07H 3/06 | (2006.01) |
| A23L 33/00 | (2016.01) |
| C07H 1/00 | (2006.01) |
| C07H 3/02 | (2006.01) |

(52) U.S. Cl.
CPC ............... C07H 3/06 (2013.01); C07H 1/00 (2013.01); C07H 3/02 (2013.01); A23L 33/40 (2016.08)

(58) Field of Classification Search
CPC .... C07H 3/06; C07H 3/02; C07H 1/00; A23L 3/44; A23L 3/46
See application file for complete search history.

(56) References Cited

U.S. PATENT DOCUMENTS

| | | |
|---|---|---|
| 7,521,212 B1 | 4/2009 | Samain et al. |
| 2007/0298116 A1 | 12/2007 | Bechtold-Peters et al. |
| 2017/0204443 A1 | 7/2017 | Baumgärtner et al. |

FOREIGN PATENT DOCUMENTS

| | | |
|---|---|---|
| CN | 102154163 A | 8/2011 |
| EP | 1405856 A1 | 4/2004 |
| EP | 2522232 A1 | 11/2012 |
| EP | 2722394 A1 | 4/2014 |
| EP | 2857410 A1 | 4/2015 |
| WO | 0104341 A1 | 1/2001 |
| WO | 2007101862 A1 | 9/2007 |
| WO | 2010070104 A1 | 6/2010 |
| WO | 2010142305 A1 | 12/2010 |
| WO | 2011100980 A1 | 8/2011 |
| WO | 2011150939 A1 | 12/2011 |
| WO | 2012112777 A2 | 8/2012 |
| WO | 2013185780 A1 | 12/2013 |
| WO | 2014009921 A2 | 1/2014 |
| WO | 2014069625 A1 | 5/2014 |
| WO | 2014075680 A1 | 5/2014 |
| WO | 2014086373 A1 | 6/2014 |
| WO | 2014153253 A1 | 9/2014 |
| WO | 2015032412 A1 | 3/2015 |
| WO | 2015032413 A1 | 3/2015 |
| WO | 2015036138 A1 | 3/2015 |
| WO | 2015049331 A1 | 4/2015 |
| WO | 2015106943 A1 | 7/2015 |
| WO | 2015150328 A1 | 10/2015 |
| WO | 2015188834 A1 | 12/2015 |
| WO | 2015197082 A1 | 12/2015 |
| WO | 2016008602 A1 | 1/2016 |
| WO | 2016086947 A1 | 6/2016 |
| WO | 2016095924 A1 | 6/2016 |
| WO | 2017101953 | 6/2017 |
| WO | 2017101958 A1 | 6/2017 |

OTHER PUBLICATIONS

Te Booy et al., Pharmaceutical Research, 1992, 9(1), p. 109-114. (Year: 1992).*
Han et al., Biotechnology Advances, 2012, 30, p. 1268-1278. (Year: 2012).*
Corbett et al., Journal of the Chemical Society, 1954, p. 1789-1791. (Year: 1954).*
Bauer, J.F., "Pharmaceutical Solids—The Amorphous Phase," Journal of Validation Technology, 2009, vol. 15(3), pp. 63-68.

(Continued)

*Primary Examiner* — Jonathan S Lau
(74) *Attorney, Agent, or Firm* — Neal, Gerber & Eisenberg LLP

(57) ABSTRACT

It is provided i) an amorphous carbohydrate with improved chemical stability and/or physical features, ii) a method for producing an amorphous carbohydrate with improved chemical stability and/or physical features, and iii) a method for improving the chemical stability and/or the physical features of an amorphous carbohydrate.

19 Claims, No Drawings

(56) References Cited

OTHER PUBLICATIONS

Baumgartner, F. et al., "Construction of *Escherichia coli* strains with chromosomally integrated expression cassettes for the synthesis of 20-fucosyllactose," Microbial Cell Factories, 2013, 13 pages. http://www.microbialcellfactories.com/content/12/1/40.

Chen, X. (2015)."Human Milk Oligosaccharides (HMOS): Structure, Function, and Enzyme-Catalyzed Synthesis," Elsevier Inc. (vol. 72), Advances in Carbohydrate Chemistry and Biochemistry, pp. 113-190. http://dx.doi.org/10.1016/bs.accb.2015.08.002.

Drouillard, S. et al., "Large-Scale Synthesis of H-Antigen Oligosaccharides by Expressing Helicobacter pylori a1,2-Fucosyltransferase in Metabolically Engineered *Escherichia coli* Cells," Angew. Chem. Int. Ed. 2006, vol. 45, pp. 1778-1780.

EFSA Scientific Panel NDA (2015). Safety of lacto-N-neotetraose as a novel food ingredient pursuant to Regulation (EC) No. 258/97. EFSA Journal, 13(7), [4183], 32 pages.

EFSA Scientific Panel NDA (2015). Safety of 2'-O-fucosyllactose as a novel food ingredient pursuant to Regulation (EC) No. 258/97. EFSA Journal, 13(7), [4184]. https://doi.org/10.2903/j.efsa.2015.4184, 32 pages.

Han, N.S. et al., "Biotechnological production of human milk oligosaccharides," Biotechnology Advances, 2012, vol. 30, pp. 1268-1278.

Kets, E.P.W. et al., "Citrate increases glass transition temperature of vitrified sucrose preparations," Cryobiology, 2004, vol. 48, pp. 46-54.

Urashima, T. et al. (2011) Nutrition and Diet Research Progress: Milk Oligosaccharides. New York: Nova Science Publishers, Inc. 92 pages.

Takamura, T. et al., "Chemical Modification of Lactose. XIII. Synthesis of Lacto-N-tetraose," Chem. Pharm. Bull., 1980, vol. 28, pp. 1804-1809.

Lee, W. et al., "Whole cell biosynthesis of a functional oligosaccharide, 2'-fucosyllactose, using engineered *Escherichia coli*," Microbial Cell Factories, 2012, 22 pages. https://doi.org/10.1186/1475-2859-11-48.

López-Sanz, S. et al., "Stability of oligosaccharides derived from lactulose during the processing of milk and apple juice," Food Chemistry, 2015, vol. 183, pp. 64-71.

Ohtake, S. et al., "Effect of pH, Counter Ion, and Phosphate Concentration on the Glass Transition Temperature of Freeze-Dried Sugar-Phosphate Mixtures," Pharmaceutical Research, 2004, vol. 21(9), pp. 1615-1621.

Priem, B. et al., "A new fermentation process allows large-scale production of human milk oligosaccharides by metabolically engineered bacteria," Glycobiology, 2002, vol. 12(4), pp. 235-240.

Samain, E. et al., "Production of O-acetylated and sulfated chitooligosaccharides by recombinant *Escherichia coli* strains harboring different combinations of nod genes," Journal of Biotechnology, 1999, vol. 72, pp. 33-47.

Ali et al., SUST Journal of Engineering and Computer Science (JECS), 2015, 16(2), 9 pages. (Year: 2015).

Kuhnert, P., Foods, 3. Food Additives, Ullmann's Enyclopedia of Industrial Chemistry, 2015 , Wiley-VCH Verlag GmbH & Co., 52 pages, First published: Jan. 28, 2016. (Year: 2016).

U.S. Appl. No. 16/630,372, filed Jan. 10, 2020.

\* cited by examiner

AMORPHOUS MIXTURE COMPRISING A NEUTRAL MONO- OR OLIGOSACCHARIDE AND AN ACIDIC NON-CARBOHYDRATE COMPONENT

CROSS-REFERENCE TO RELATED APPLICATION

This application is a divisional of U.S. patent application Ser. No. 16/630,372, filed on Jan. 10, 2020, which is a national stage entry pursuant to 35 U.S.C. § 371 of International Application No. PCT/IB2018/055136, filed on Jul. 12, 2018, which claims priority to Denmark Patent Application No. PA 2017 70567, filed Jul. 12, 2017, the contents of all of which are fully incorporated herein by reference.

FIELD OF THE INVENTION

The present invention relates to amorphous, preferably spray-dried or freeze-dried compositions comprising neutral oligosaccharides, advantageously human milk oligosaccharides, and a method for increasing the stability of amorphous neutral oligosaccharides.

BACKGROUND OF THE INVENTION

In recent years, the manufacture and commercialization of complex carbohydrates including naturally secreted oligosaccharides have increased significantly due to their roles in numerous biological processes occurring in living organisms. Secreted oligosaccharides such as human milk oligosaccharides (HMOs) are carbohydrates which have gained much interest in recent years and are becoming important commercial targets for nutrition and therapeutic industries. In particular, the synthesis of these HMOs has increased significantly due to the role of HMOs in numerous biological processes occurring in humans. The great importance of HMOs is directly linked to their unique biological activities such as antibacterial, antiviral, immune system and cognitive development enhancing activities. Human milk oligosaccharides are found to act as prebiotics in the human intestinal system helping to develop and maintain the intestinal flora. Furthermore, they have also proved to be anti-inflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Likewise, the compounds are also of interest in the medicinal industry for the production of therapeutics due to their prognostic use as immunomodulators. To date, the structures of more than 140 HMOs have been determined (see Urashima et al.: *Milk Oligosaccharides*, Nova Biomedical Books, New York, 2011; Chen *Adv. Carbohydr. Chem. Biochem.* 72, 113 (2015)), and considerably more are probably present in human milk.

Low cost ways have been sought for making industrial quantities of as many as possible of the HMOs, so that their uses in nutritional and therapeutic formulations for infants, as well as possibly children and adults, could be discovered, developed and exploited by researchers worldwide. Biotechnological approaches have proved to be promising and cost-efficient for the synthesis of a variety of HMOs. Precisely, HMOs can be produced in aqueous media by fermentation of genetically modified bacteria, yeasts or other microorganisms. See, for example, WO 01/04341, WO 2007/101862, WO 2010/070104, WO 2010/142305, WO 2012/112777, WO 2014/153253, WO 2015/032412, WO 2015/032413, WO 2015/036138, WO 2015/150328, WO 2015/197082, WO 2016/008602, WO 2017/101958, EP-A-2722394, Priem et al. *Glycobiology* 12, 235 (2002), Drouillard et al. *Angew. Chem. Int. Ed.* 45, 1778 (2006), Han et al. *Biotechnol. Adv.* 30, 1268 (2012), Lee et al. *Microb. Cell Fact.* 11:48 (2012) and Baumgärtner et al. *Microb. Cell Fact.* 12:40 (2013). Chemical and ex vivo enzymatic syntheses of HMOs are also known.

The final step of the above technologies is often crystallization or recrystallization of the individual HMOs from aqueous organic solvent such as an alcohol, usually methanol (see for example WO 2011/100980, WO 2011/150939, WO 2014/009921, WO 2014/075680, WO 2014/086373, WO 2014/069625, WO 2015/188834, WO 2016/086947, WO 2016/095924, EP-A-1405856, Kuhn et al. *Chem. Ber.* 95, 513 and 518 (1962), Takamura et al. *Chem. Pharm. Bull.* 28, 1804 (1980)). On the other hand, HMOs may be provided in solid form other than crystalline, e.g. as spray-dried or freeze-dried amorphous powder (see for example WO 2013/185780, WO 2015/049331, WO 2015/106943, CN 102154163 A). The properties of a crystalline and an amorphous substance are different. While the amorphous form of a substance is, in general, expected to show better solubility and bioavailability, its crystalline counterpart is chemically and physically more stable and less hygroscopic (Bauer *J. Valid. Technol.* 63 (Summer 2009)).

Therefore there is a need to improve the chemical stability and/or the physical features of an amorphous carbohydrate, preferably neutral HMO, while its beneficial properties are maintained.

SUMMARY OF THE INVENTION

It is the object of the present invention to provide i) an amorphous carbohydrate with improved chemical stability and/or physical features, ii) a method for producing an amorphous carbohydrate with improved chemical stability and/or physical features, and iii) a method for improving the chemical stability and/or the physical features of an amorphous carbohydrate.

Accordingly, the first aspect of the invention relates to an amorphous mixture comprising a neutral mono- or oligosaccharide and an acidic non-carbohydrate component, wherein the pH of said mixture in its 5 w/w % aqueous solution is around 3.5-5.8. Preferably, the amorphous mixture is a spray-dried or freeze-dried mixture, more preferably spray-dried.

Also preferably, the amorphous mixture consists essentially of one or more neutral mono- or oligosaccharides and one or more acidic non-carbohydrate components.

The second aspect of the invention relates to a method for making an amorphous mixture comprising a neutral mono- or oligosaccharide and an acidic non-carbohydrate component, wherein the pH of said mixture in its 5 w/w % aqueous solution is around 3.5-5.8, comprising the steps of a) preparing an aqueous solution of said neutral mono- or oligosaccharide, b) adding an acidic non-carbohydrate component to said aqueous solution so that the pH is not lower than $-\log(x/5 \cdot 10^{-3.5})$ and not higher than $-\log(x/5 \cdot 10^{-5.8})$, wherein x is the concentration of the neutral mono- or oligosaccharide in said aqueous solution in w/w %, then c) spray-drying or freeze-drying, preferably spray-drying, the pH adjusted solution obtained in step b).

The third aspect of the invention relates to a use of an acidic component for improving the chemical stability and/or the physical properties of an amorphous neutral mono- or oligosaccharide, comprising mixing the acidic component and said neutral mono- or oligosaccharide in an aqueous solution and spray-drying or freeze-drying, preferably spray-drying.

DETAILED DESCRIPTION OF THE INVENTION

Terms and Definitions

The term "monosaccharide" means a sugar of 5-9 carbon atoms that is an aldose (e.g. D-glucose, D-galactose, D-mannose, D-ribose, D-arabinose, L-arabinose, D-xylose, etc.), a ketose (e.g. D-fructose, D-sorbose, D-tagatose, etc.), a deoxysugar (e.g. L-rhamnose, L-fucose, etc.) or a deoxy-aminosugar (e.g. N-acetylglucosamine, N-acetylmannosamine, N-acetylgalactosamine, etc.). "Neutral monosaccharide" means a monosaccharide that lacks acidic or basic functional groups in free or salt form. In this regard, for example, an uronic acid, a ketoaldonic acid (e.g. sialic acid) or a deoxyamino sugar with free amino group (e.g. glucosamine) are not considered to be a neutral monosaccharide. Once those functional groups are modified so that they are not able to form an acid addition salt any longer (due to e.g. esterification of the carboxyl group or N-acylation of the amino group), the monosaccharide bearing such group is considered neutral.

The term "oligosaccharide" means a sugar polymer consisting of at least two, preferably from three to eight, more preferably from three to six, monosaccharide units (vide supra). The tri- or higher oligosaccharide can have a linear or branched structure containing monosaccharide units that are linked to each other by interglycosidic linkages. "Neutral oligosaccharide" is an oligosaccharide consisting of neutral monosaccharide units.

The term "human milk oligosaccharide" or "HMO" means a complex carbohydrate found in human breast milk (Urashima et al.: *Milk Oligosaccharides*, Nova Medical Books, N Y, 2011; Chen *Adv. Carbohydr. Chem. Biochem.* 72, 113 (2015)). The neutral HMOs have a core structure being a lactose unit at the reducing end that is elongated by one or more β-N-acetyl-lactosaminyl and/or one or more β-lacto-N-biosyl units, and which core structures can be substituted by an α-L-fucopyranosyl moiety. In this regard, this non-acidic (or neutral) HMOs are devoid of a sialyl residue. The non-acidic (or neutral) HMOs can be fucosylated or non-fucosylated. Examples of such neutral non-fucosylated HMOs include lacto-N-triose II (LNTri II, GlcNAc(β1-3)Gal(β1-4)Glc), lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-1), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-1), fucosyl-para-lacto-N-neohexaose II (F-pLNnH II) and fucosyl-lacto-N-neohexaose (FLNnH). Preferably, lactose is not considered to be an HMO.

The term "around" means, in one embodiment, 10% deviation from the value indicated, or in another embodiment, ±5% deviation.

Amorphous Mono- or Oligosaccharides with Improved Stability

Although an amorphous compound, especially a hydrophilic compound, generally shows better water solubility, higher dissolution rate and better bioavailability, which are key features in product development in the pharma and food industry, its shelf-life is expected to be shorter than that of the corresponding crystalline form. The amorphous compounds tend to undergo chemical degradation in higher degree than their crystalline form, and their physical appearance may change disadvantageously, e.g. due to agglutination. The present inventors noticed that in samples of spray-dried neutral oligosaccharides with aldose reducing terminal, upon prolonged storage, a new carbohydrate type by-product appeared, the amount of which in the sample increased as a function of time. As a result of careful analysis, this contamination proved to be a rearranged ketose derivative of the reducing oligosaccharide, which rearrangement can be illustrated on an aldohexose as follows:

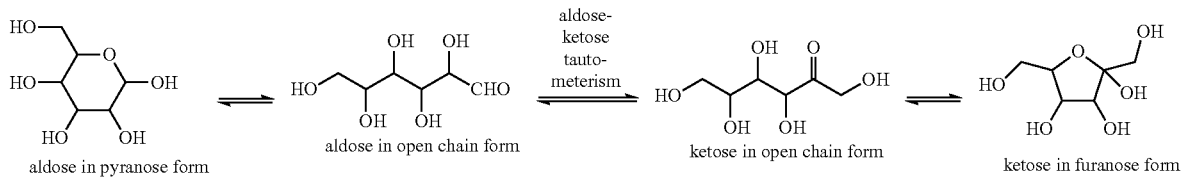 [SMILES: OCC1OC(O)C(O)C(O)C1O ; O=CC(O)C(O)C(O)C(O)CO ; O=C(CO)C(O)C(O)C(O)CO ; OCC1OC(O)(CO)C(O)C1O]

The present inventors surprisingly found that the above rearrangement does not occur, or at least occurs to a significantly lower degree, in solid state if the spray-dried or freeze-dried amorphous neutral oligosaccharide contains an acidic component. In this regard the chemical stability of the spray-dried or freeze-dried material can even reach that of the corresponding crystalline form.

Accordingly, the first aspect of the invention is to provide an amorphous mixture comprising a neutral mono- or oligosaccharide and an acidic non-carbohydrate component, wherein the pH of said mixture in its 5 w/w % aqueous solution is around 3.5-5.8.

The amorphous mixture, in one embodiment, is a spray-dried mixture, in other embodiment, is a freeze-dried mixture.

Preferably, the neutral mono- or oligosaccharide is a reducing mono- or oligosaccharide.

In one embodiment, the monosaccharide or the monosaccharide unit at the reducing end of said neutral oligosaccharide is an aldose. In other embodiment, the monosaccharide or the monosaccharide unit at the reducing end of said neutral oligosaccharide is a ketose.

Also preferably, in another embodiment, the monosaccharide unit at the reducing end of the neutral oligosaccharide is glucose, more preferably a galactose unit is attached to said glucose with a β1-4 interglycosidic linkage to form a lactose moiety.

In a preferred embodiment, the reducing neutral oligosaccharide is a tri- or higher neutral oligosaccharide, advantageously having a lactose moiety at the reducing end.

Particularly, the tri- or higher neutral oligosaccharide comprising a lactose moiety at the reducing end is a neutral human milk oligosaccharide (HMO). The neutral HMO is preferably a tri- to octasaccharide HMO, more preferably a tri-, tetra-, penta- or hexasaccharide HMO. More preferably, trisaccharide HMO can be selected from the group consisting of 2'-O-fucosyllactose (2'-FL), 3-O-fucosyllactose (3-FL) and lacto-N-triose II (LNTri II, GlcNAc(β1-3)Gal(β1-4)Glc); tetrasaccharide HMO can be selected from the group consisting of lacto-N-tetraose (LNT), lacto-N-neotetraose (LNnT) and difucosyllactose (lacto-difuco-tetraose, DFL); pentasaccharide HMO can be selected from the group consisting of lacto-N-fucopentaose I (LNFP-1, Fucα1-2Galβ1-3GlcNAcβ1-3Galβ1-4Glc), lacto-N-fucopentaose VI (LNFP-VI, Galβ1-4GlcNAcβ1-3Galβ1-4[Fucα1-3]Glc), lacto-N-fucopentaose II (LNFP-II, Galβ1-3[Fucα1-4]GlcNAcβ1-3Galβ1-4Glc), lacto-N-fucopentaose III (LNFP-III, Galβ1-4[Fucα1-3]GlcNAcβ1-3Galβ1-4Glc), lacto-N-fucopentaose V (LNFP-V, Galβ1-3GlcNAcβ1-3Galβ1-4[Fucα1-3]Glc); hexasaccharide HMO can be selected from the group consisting of lacto-N-hexaose (LNH, Galβ1-3GlcNAcβ1-3[Galβ1-4GlcNAcβ1-6]Galβ1-4Glc), lacto-N-neohexaose (LNnH, Galβ1-4GlcNAcβ1-3[Galβ1-4GlcNAcβ1-6]Galβ1-4Glc), para-lacto-N-hexaose (pLNH, Galβ1-3GlcNAcβ1-3Galβ1-4GlcNAcβ1-3Galβ1-4Glc), para-lacto-N-hexaose II (pLNH II, Galβ1-3GlcNAcβ1-3Galβ1-3GlcNAcβ1-3Galβ1-4Glc), para-lacto-N-neohexaose (pLNnH, Galβ1-4GlcNAcβ1-3Galβ1-4GlcNAcβ1-3Galβ1-4Glc), LNDFH II (Galβ1-3[Fucα1-4]GlcNAcβ1-3Galβ1-4[Fucα1-3]Glc), LNDFH III (Galβ1-4[Fucα1-3]GlcNAcβ1-3Galβ1-4[Fucα1-3]Glc), para-lacto-N-neohexaose II (pLNnH II, Galβ1-3GlcNAcβ1-3Galβ1-4GlcNAcβ1-3Galβ1-4Glc)).

In other context, the neutral HMO is a non-fucosylated HMO, a monofucosylated HMO or a multifucosylated HMO. A non-fucosylated HMO, preferably, can be lacto-N-triose II, LNT, LNnT, LNH, L:NnH, pLNH, pLNH II, pLNnH or pLNnH II. A monofucosylated HMO, preferably, can be 2'-FL, 3-FL, LNFP-I, LNFP-II, LNFP-III, LNFP-V or LNFP-VI. A multifucosylated HMO is, particularly, a difucosylated or a trifucosylated HMO, example of a difucosylated HMO is DFL, LNDFH II or LNDFH III.

The acidic non-carbohydrate component in the amorphous, preferably in the spray-dried or freeze-dried mixture defined above is an inorganic acid or an organic compound having an acidic character different than a carbohydrate. Preferably, suitable inorganic and organic acids are those that are known as having no safety concern when applied in the pharma and food industry, for example those generally used for making a pharmaceutically acceptable acid-addition salt of an active pharmaceutical ingredient with basic character. Inorganic acid can be selected from e.g. sulfuric acid and its monosalts (like monosodium sulphate), HCl, HBr, nitric acid, phosphoric acid and its mono- and disalts (like monosodium phosphate or disodium phosphate) or perchloric acid. Also preferably, suitable organic acids are alkanoic acids like formic acid, acetic acid or propionic acid, alkanoic diacids like oxalic acid, malonic acid or succinic acid, hydroxy acids like tartaric acid, lactic acid or malic acid, tricarboxylic acids like citric acid.

In one embodiment, the amorphous, preferably the spray-dried or freeze-dried mixture may comprise more than one neutral HMO, such as two, three, four, five, two to six, three to ten neutral HMOs. Also, the amorphous, preferably the spray-dried or freeze-dried mixture may contain more than one acidic non-carbohydrate component.

In a preferred embodiment, the amorphous, preferably the spray-dried or freeze-dried mixture defined above consists essentially of one or more neutral mono- or oligosaccharides, advantageously HMOs as disclosed above, and one or more acidic non-carbohydrate components.

Forced stability comparison tests at high temperatures showed that the presence of the acidic non-carbohydrate component in the spray-dried HMOs practically prevented the formation of the rearranged ulose. In this regard the spray-dried HMO was chemically as stable as the corresponding HMO in crystalline form.

The pH of the claimed amorphous, preferably the spray-dried or freeze-dried mixture in its 5 w/w % aqueous solution should be not higher than around 5.8. A pH higher than this is very close to the neutral region, at which, according to the comparison tests, the aldose-ketose rearrangement can easily occur. On the other hand, it is advisable that the pH, as defined above, is not lower than 3.5. A pH lower than 3.5 may initiate the an acid catalysed degradation of the oligosaccharide by hydrolysing at least one of the interglycosidic linkages. Therefore it is preferred when the pH of the solution is between 4.0-5.8, such as 4.2-5.8, 4.5-5.8, 4.0-5.5, 4.2-5.5, 4.0-5.5, 4.2-5.5, 4.5-5.5, 4.0-5.0, 4.2-5.0 or 4.5-5.0, another preferred pH range is 5.0-5.8, such as 5.0-5.5 or 5.5-5.8.

In one embodiment, when the neutral HMO or at least one of the neutral HMOs in the amorphous, preferably the spray-dried or freeze-dried mixture is 2'-FL, the preferred pH is not less than 4.5, that is the pH range can be 4.5-5.8, 4.5-5.5, 4.5-5.0, 5.0-5.8, 5.0-5.5 or 5.5-5.8, preferably 5.2-5.8, because due to the acid susceptibility of the α1,2-fucosyl moiety, a low degree of hydrolysis to fucose and lactose at around a pH of 3.5 can be observed, which hydrolysis, though in smaller extent, is still detectable at a pH around 4.0-4.5 too. This means that an amorphous 2'-FL according to the present invention, the pH of the 5 w/w % aqueous solution of which is around 3.5-4.5, has a slightly shorter shelf-life than that for an amorphous 2'-FL having a pH of 4.5-5.8. However DFL, also having an α1,2-fucosyl moiety in its structure, proved to be hydrolytically stabile at a pH range of 3.5-4.5. In this regard it can be concluded that a fucosylated neutral HMO other than 2'-FL is hydrolytically as stable as a non-fucosylated neutral HMO.

In other embodiment, the neutral HMO in the amorphous mixture according to the invention is 3-FL or DFL, and the preferred pH its 5 w/w % aqueous solution is 4.0-5.8, such as 4.2-5.8, 4.5-5.8, 4.0-5.5, 4.2-5.5, 4.0-5.5, 4.2-5.5, 4.5-5.5, 4.0-5.0, 4.2-5.0 or 4.5-5.0, another preferred pH range is 5.0-5.8, such as 5.0-5.5 or 5.5-5.8.

In other embodiment, the neutral oligosaccharide in the amorphous mixture according to the invention is a mono- or difucosylated tetrasaccharide, such as a mono- or difucosylated LNT or LNnT, and the preferred pH its 5 w/w % aqueous solution is 4.0-5.8, such as 4.2-5.8, 4.5-5.8, 4.0-5.5, 4.2-5.5, 4.0-5.5, 4.2-5.5, 4.5-5.5, 4.0-5.0, 4.2-5.0 or 4.5-5.0, another preferred pH range is 5.0-5.8, such as 5.0-5.5 or 5.5-5.8. Examples of monofucosylated LNT or LNnT are LNFP-I, LNFP-II, LNFP-III, LNFP-V or LNFP-VI. Examples of difucosylated LNT or LNnT are LNDFH II or LNDFH III.

In other embodiment, the neutral HMO in the amorphous mixture according to the invention is LNT, and the preferred pH its 5 w/w % aqueous solution is 4.0-5.8, such as 4.2-5.8, 4.5-5.8, 4.0-5.5, 4.2-5.5, 4.0-5.5, 4.2-5.5, 4.5-5.5, 4.0-5.0, 4.2-5.0 or 4.5-5.0, another preferred pH range is 5.0-5.8, such as 5.0-5.5 or 5.5-5.8.

In other embodiment, the neutral HMO in the amorphous mixture according to the invention is LNnT, and the preferred pH its 5 w/w % aqueous solution is 4.0-5.8, such as 4.2-5.8, 4.5-5.8, 4.0-5.5, 4.2-5.5, 4.0-5.5, 4.2-5.5, 4.5-5.5, 4.0-5.0, 4.2-5.0 or 4.5-5.0, another preferred pH range is 5.0-5.8, such as 5.0-5.5 or 5.5-5.8.

The second aspect of the invention relates to a method for making an amorphous mixture comprising a neutral mono- or oligosaccharide and an acidic non-carbohydrate component, wherein the pH of said mixture in its 5 w/w % aqueous solution is around 3.5-5.8, comprising the steps of
a) preparing an aqueous solution of said neutral mono- or oligosaccharide,
b) adding an acidic non-carbohydrate component to said aqueous solution so that the pH is not lower than $-\log(x/5 \cdot 10^{-3.5})$ and not higher than $-\log(x/5 \cdot 10^{-5.8})$, wherein x is the concentration of the neutral mono- or oligosaccharide in said aqueous solution after step a) in w/w %, then
c) spray-drying or freeze-drying the pH adjusted solution obtained in step b).

In step a) of the method, an aqueous solution of one of more neutral mono- or oligosaccharides is made in a conventional manner. It is preferred when the solution is clear and the neutral mono- or oligosaccharide(s) is/are dissolved. The one of more neutral mono- or oligosaccharides, before addition of water to it/them or adding it/them to water, may be in any solid form (for example, crystalline, amorphous [precipitated, freeze-dried, spray-dried] or mixture thereof), in syrupy form or even in an aqueous solution. The one of more neutral mono- or oligosaccharides, before conducting step a), may contain some amounts or a residual amount of (volatile) organic solvent(s), because those solvents are substantially removed in step c) of the method and will not be comprised in the amorphous final substance. Preferably, the one of more neutral mono- or oligosaccharides, before conducting step a), do not contain substantial amount of acidic or basic contaminant. If they do, less (in case of acidic contamination) or more (in case of basic contamination) acidic non-carbohydrate component may be added to reach the required pH range.

In step b) of the method, the acidic non-carbohydrate component is added to the solution obtained in step a). It is preferred, that the concentration of the mono- or oligosaccharide(s) in the solution is practically not diluted by the addition of the acidic component, which means that the concentration of the mono- or oligosaccharide solution in step a) and after the addition of the acidic component in step b) is practically the same. This can be achieved when the acidic component, if solid, is added in its solid form or in its concentrated aqueous solution, or if liquid or gaseous, in its concentrated aqueous solution. Should the mono- or oligosaccharide solution be diluted noticeably during the addition of the acidic component, the value x in step b) corresponds to the concentration of the mono- or oligosaccharide after dilution. In any of the cases, the acid is added slowly, preferably under stirring, to the aqueous solution of the mono- or oligosaccharide, and the pH is continuously checked e.g. by a pH-meter. If the required pH is achieved, the addition of acid is terminated. It is also preferred that concentration x is close to 5 w/w %. However, for economical reason, the concentration x can be significantly higher than 5 w/w %, for example 20-50 w/w %, around 25 w/w %, around 30 w/w %, around 35 w/w % or around 40 w/w %.

In step c), the aqueous solution obtained in step b) is spray-dried in a conventional way: the resulting aqueous solution can be spray-dried with hot air or hot inert gas, preferably hot air, at about 130-210° C., preferably 140 to 180° C., to produce a substantially dry, amorphous, free-flowing powder of the mixture comprising or consisting essentially of a neutral HMO and the acidic component. In this regard, any conventional spray-drying apparatus can be used, such as a co-current or a multiple effect spray-dryer, preferably a two-stage spray dryer (with a fluid bed attachment). Likewise, the choice of the atomizer or spray nozzle in the spray-dryer is not considered critical, and any common rotary disk or high pressure swirl nozzle can be suitably utilized. Alternatively, the aqueous solution obtained in step b) is freeze-dried in a conventional way.

The third aspect of the invention relates to a use of an acidic non-carbohydrate component for improving the chemical stability and/or the physical properties of an amorphous neutral mono- or oligosaccharide, comprising mixing the acidic component and said neutral mono- or oligosaccharide in an aqueous solution and spray-drying or freeze-drying said aqueous solution to obtain an amorphous mixture containing, preferably consisting essentially of, one or more neutral mono- or oligosaccharides and one or more acidic non-carbohydrate components.

The term "improving the chemical stability of an amorphous neutral mono- or oligosaccharide" preferably means that said amorphous mono- or oligosaccharide is less prone to undergo chemical degradation or rearrangement reaction in the presence of the acidic non-carbohydrate component than in its absence under the same conditions, therefore these features are ameliorated. Example of chemical degradation is hydrolytic decomposition through breaking at least one of the interglycosidic linkages; example of chemical rearrangement is a rearrangement of an aldose to ketose or of a ketose to aldose.

The term "improving the physical properties of an amorphous neutral mono- or oligosaccharide" preferably means that said amorphous mono- or oligosaccharide shows better physical properties in the presence of the acidic non-carbohydrate component than in its absence under the same conditions, therefore these properties are ameliorated. Examples of improved physical properties are lower propensity for phase change (e.g. vitrification, crystallization) or lower degree of agglutination.

The present inventors surprisingly discovered that the chemical stability of an amorphous spray-dried neutral mono- or oligosaccharide could be improved if an acidic component other than a carbohydrate was added to the mono- or oligosaccharide. This is achieved when one or more neutral mono- or oligosaccharides and one or more acidic non-carbohydrate components, preferably only one acidic component, are dissolved in water and the obtained solution is spray-dried or freeze-dried. The preferred and more preferred embodiments concerning the neutral mono- or oligosaccharide, the acidic component and the obtainable spray-dried or freeze-dried mixture are disclosed in the first aspect of the invention; and the preferred and more preferred embodiments concerning the method of making the spray-dried or freeze-dried mixture are disclosed in the second aspect of the invention.

The fourth aspect of the invention relates to an amorphous mixture containing, preferably consisting essentially of, one or more neutral mono- or oligosaccharides and one or more acidic non-carbohydrate components obtainable by method disclosed in the second aspect of the invention.

A fifth aspect of the invention relates to a method for improving the chemical stability and/or the physical properties of an amorphous neutral mono- or oligosaccharide, the method comprising
- a) preparing an aqueous solution of said neutral mono- or oligosaccharide,
- b) adding an acidic non-carbohydrate component to said aqueous solution so that the pH is not lower than $-\log(x/5 \cdot 10^{-3.5})$ and not higher than $-\log(x/5 \cdot 10^{-5.8})$, wherein x is the concentration of the neutral mono- or oligosaccharide in said aqueous solution after step a) in w/w %,
- c) spray-drying or freeze-drying, preferably spray-drying, the pH adjusted solution obtained in step b), and
- d) obtaining an amorphous mixture containing, preferably consisting essentially of, said neutral mono- or oligosaccharide and said acidic non-carbohydrate component.

In the fifth aspect of the invention, the preferred and more preferred embodiments concerning the neutral mono- or oligosaccharide, the acidic component and the obtainable spray-dried or freeze-dried mixture are disclosed in the first aspect of the invention; and the preferred and more preferred embodiments concerning the method of making the spray-dried or freeze-dried mixture are disclosed in the second aspect of the invention.

EXAMPLES

Example 1

2'-FL was made by bacterial fermentation and isolated as disclosed in WO 2015/032412. The substance contained DFL as accompanying HMO. An aqueous solution was made the concentration of which concerning (2'-FL+DFL) was 34.5 g/100 g solution.

Sample A: a part of the aqueous solution was adjusted to pH of 3.2 in environmental conditions (i.e., at room temperature and under standard pressure) by addition of 25% of aqueous sulfuric acid solution. The so-obtained acidic solution was spray-dried on a Buchi minispray dryer B290 (inlet temperature: 175° C., outlet temperature: 120° C.) to give a white amorphous powder. The pH of its 5 w/w % solution was 4.2.

Sample B: a part of the aqueous solution was spray-dried on a Buchi minispray dryer B290 (inlet temperature: 175° C., outlet temperature: 120° C.) to give a white amorphous powder. The pH of its 5 w/w % solution was 6.3.

Sample C: a part of the aqueous solution was concentrated until around 55% of its weight. Then methanol was added to crystallize 2'-FL which was obtained as a white crystalline material after washing and drying (see WO 2015/188834). The pH of its 5 w/w % solution was 6.4.

One gram of each sample, separately, was put into a 4 ml glass vial and closed with screw lid containing teflon inliner. The 8-week storage sample was put into a 60° C. oven, followed by the 4-week and the 2-week samples 4 and 6 weeks later, respectively), so the incubation of all samples ended in the same time. Similar pattern of experimental design was followed with the samples to be measured at 80° C. (4-week, 2-week and 1-week samples). The samples were kept in a freezer until they were put into the oven at a given time. Standards were kept in a freezer until analysis.

The samples did not show phase change during investigation.

The stability samples and the standards were analysed by HPAEC.

The table below shows the content of 2'-O-fucosyl-lactulose, a ketose rearranged derivative of 2'-FL, in the samples (in w/w %).

|  | sample A (amorphous, pH = 4.2) | sample B (amorphous, pH = 6.3) | sample C (crystalline, pH = 6.4) |
| --- | --- | --- | --- |
| t = 0 | 0.92 | 0.95 | 0.43 |
| 60° C., 2 weeks | 0.98 | 1.02 | 0.47 |
| 60° C., 4 weeks | 0.94 | 0.99 | 0.46 |
| 60° C., 8 weeks | 0.92 | 1.00 | 0.44 |
| 80° C., 1 weeks | 0.92 | 1.04 | 0.44 |
| 80° C., 2 weeks | 0.92 | 1.09 | 0.45 |
| 80° C., 4 weeks | 0.95 | 1.13 | 0.45 |

The amorphous samples having acidic pH showed practically no 2'-O-fucosyl-lactulose isomerisation during the storage under forced conditions, while in those having a close to neutral pH an increasing amount of the rearranged derivative was observed. In this regard, the behaviour of amorphous samples having acidic pH was the same as that of the crystalline samples.

Example 2

A mixture of 2'-FL and DFL was made by bacterial fermentation and isolated as disclosed in WO 2015/032412. The DFL content was about 14 w/w %. An aqueous solution was made the concentration of which concerning (2'-FL+DFL) was 25 g/100 g solution.

Sample A: a part of the aqueous solution was adjusted to pH of 3.7 in environmental conditions (i.e., at room temperature and under standard pressure) by addition of 25% of aqueous sulfuric acid solution. The so-obtained acidic solution was spray-dried on a Buchi minispray dryer B290 (inlet temperature: 175° C., outlet temperature: 116° C.) to give a white amorphous powder. The pH of its 5 w/w % solution was 4.5.

Sample B: a part of the aqueous solution was spray-dried on a Buchi minispray dryer B290 (inlet temperature: 175° C., outlet temperature: 120° C.) to give a white amorphous powder. The pH of its 5 w/w % solution was 7.0.

One gram of each sample, separately, was put into a 4 ml glass vial and closed with screw lid containing teflon inliner. The 8-week storage sample was put into a 60° C. oven, followed by the 4-week and the 2-week samples 4 and 6 weeks later, respectively), so the incubation of all samples ended in the same time. Similar pattern of experimental design was followed with the samples to be measured at 80° C. (4-week, 2-week and 1-week samples). The samples were kept in a freezer until they were put into the oven at a given time. Standards were kept in a freezer until analysis.

The samples did not show phase change during investigation.

The stability samples and the standards were analysed by HPAEC.

The table below shows the content of 2'-O-fucosyl-lactulose and 3,2'-di-O-fucosyl-lactulose, the ketose rearranged derivatives of 2'-FL and DFL, respectively, in the samples (in w/w %).

|  | sample A (pH = 4.5) | | sample B (pH = 7.0) | |
| --- | --- | --- | --- | --- |
|  | 2'-O-fucosyl-lactulose | 3,2'-di-O-fucosyl-lactulose | 2'-O-fucosyl-lactulose | 3,2'-di-O-fucosyl-lactulose |
| t = 0 | 0.16 | 0.01 | 0.24 | 0.02 |
| 60° C., 2 weeks | 0.17 | 0.01 | 0.37 | 0.05 |
| 60° C., 4 weeks | 0.19 | 0.01 | 0.43 | 0.06 |
| 60° C., 8 weeks | 0.19 | 0.01 | 0.45 | 0.06 |
| 80° C., 1 weeks | 0.17 | 0.01 | 0.51 | 0.07 |
| 80° C., 2 weeks | 0.18 | 0.01 | 0.65 | 0.10 |
| 80° C., 4 weeks | 0.18 | 0.02 | 0.69 | 0.10 |

The amorphous samples having acidic pH showed practically no 2'-O-fucosyl-lactulose and 3,2'-di-O-fucosyl-lactulose isomerisation during the storage under forced conditions, while in those having a neutral pH an increasing amounts of the rearranged derivatives was observed.

A slight hydrolysis of 2'-FL into fucose and lactose in the acidic samples was observed, whereas such hydrolysis did not occur in the neutral sample. On the other hand, DFL did not undergo hydrolysis either the acidic or the neutral sample. This data indicate that the preferred pH range for 2'-FL, in which no substantial hydrolysis and rearrangement occur, can be estimated as 5.2-5.8.

Example 3

LNT was made by fermentation using an *Escherichia coli* K12 strain DH1, obtained from the Deutsche Sammlung von Mikroorganismen (reference DSM 5346), in which following genes were deleted: nadC, lacZ, nanKETA, lacA, lacI, melA, wcaJ and mdoH, while maintaining genes involved in the UDP-GlcNAc and UDP-Gal biosynthesis. The strain furthermore contained a *N. meningitidis* IgtA gene for β-1,3-N-acetylglucosaminyl transferase integrated in the genome of the strain and plasmid carrying *Helicobacter pylori* ATCC 43504 galTK gene for β-1,3-galactosyl transferase and the native regulatory and coding sequence of nadC. Fermentation parameters for a 2 l fermenter: 0.6 l of aqueous minimal culture medium (Samain et al. *J. Biotechnol.* 72, 33 (1999) is placed in a fermenter, the temperature is kept at 28° C. and the pH is regulated at 6.8 with 28% $NH_4OH$. The inoculum of the strain is in a defined minimal medium (20 ml) supplemented with trace minerals. The exponential growth phase starts with the inoculation and stops when the glucose carbon source, initially added to the aqueous culture medium, is exhausted. A feeding solution of glucose (750 g/l) is added to the culture medium with a feed rate of 7 ml/h. Lactose is added in two portions: 80 g in 160 ml water after 1 hour, then 40 g in 80 ml of water after 42 hours. The fermentation lasts for about 85-95 hours and produces a final aqueous culture medium containing LNT accompanied by LNTri II, pLNH II and remaining lactose (LNT titre: 40-45 g/l).

The fermentation broth was ultrafiltered to separate the biomass and/or high molecular weight suspended solids from soluble components of the broth thus to obtain an UF permeate that contained LNT and accompanying carbohydrates, which UF permeate was nanofiltered to obtain the NF retentate that contained LNT and accompanying carbohydrates. The UF permeate was purified with a strong cation exchange resin in $H^+$-form directly followed by a treatment with a weak anion exchange resin in free base form. The combined neutralized fractions containing LNT and the accompanying carbohydrates were treated with active charcoal to give a clear solution.

Sample A: the above aqueous solution (25.4 g of LNT+2 g of LNTri II+0.9 g of pLNH II+2 g of lactose/100 g solution) was adjusted to pH of 3.2 in environmental conditions (i.e., at room temperature and under standard pressure) by addition of 25% of aqueous sulfuric acid solution.

The so-obtained acidic solution was spray-dried on a Buchi minispray dryer B290 (inlet temperature: 175° C., outlet temperature: 109° C.) to give a white amorphous powder. The pH of its 5 w/w % solution was 4.5.

Sample B: the above aqueous solution (25.4 g of LNT+2 g of LNTri II+0.9 g of pLNH II+2 g of lactose/100 g solution) was spray-dried on a Buchi minispray dryer B290 (inlet temperature: 175° C., outlet temperature: 112° C.) to give a white amorphous powder. The pH of its 5 w/w % solution was 6.8.

Sample C: LNT polymorph C was prepared according to WO 2017/101953. The pH of its 5 w/w % solution was 6.3.

One gram of each sample, separately, was put into a 4 ml glass vial and closed with screw lid containing teflon inliner. The 8-week storage sample was put into a 60° C. oven, followed by the 4-week and the 2-week samples 4 and 6 weeks later, respectively), so the incubation of all samples ended in the same time. Similar pattern of experimental design was followed with the samples to be measured at 80° C. (4-week, 2-week and 1-week samples). The samples were kept in a freezer until they were put into the oven at a given time. Standards were kept in a freezer until analysis.

The samples did not show phase change during investigation.

The stability samples and the standards were analysed by HPAEC.

The table below shows the content of the ketose rearranged derivative of LNT (3Galβ1-3GlcNAcβ1-3Galβ1-4Fru) in the samples (in w/w %).

|  | sample A (amorphous, pH = 4.5) | sample B (amorphous, pH = 6.8) | sample C (crystalline, pH = 6.3) |
| --- | --- | --- | --- |
| t = 0 | 0.70 | 0.72 | 0.12 |
| 60° C., 2 weeks | 0.73 | 0.82 | 0.13 |
| 60° C., 4 weeks | 0.69 | 0.87 | 0.20 |
| 60° C., 8 weeks | 0.74 | 0.92 | 0.22 |
| 80° C., 1 weeks | 0.63 | 0.91 | 0.23 |
| 80° C., 2 weeks | 0.67 | 1.00 | 0.29 |
| 80° C., 4 weeks | 0.71 | 1.09 | 0.28 |

The amorphous samples having acidic pH showed practically no rearrangement during the storage under forced conditions, while in those having neutral pH, as well as in the crystalline samples increasing amounts of the rearranged derivative were observed. In this regard, the behaviour of the amorphous samples having acidic pH was more beneficial than that of any of the neutral amorphous or crystalline samples.

No significant hydrolysis products were detected in all three samples.

The invention claimed is:
1. A method of preparing an amorphous mixture, comprising:
   a) preparing an aqueous solution of one or more neutral mono- or oligosaccharides,
   b) adding one or more acidic non-carbohydrate components to the aqueous solution so that the pH is not lower than $-\log(x/5\cdot 10^{-3.5})$ and not higher than $-\log(x/5\cdot 10^{-5.8})$, wherein x is the concentration of the one or more neutral mono- or oligosaccharides in said aqueous solution after step a) in w/w %, c) spray-drying or freeze-drying the solution obtained in step b), and d) obtaining the amorphous mixture comprising the one or more neutral mono- or oligosaccharides and the one or more acidic non-carbohydrate components, wherein the mono- or oligosaccharide is a reducing mono- or oligosaccharide and the reducing monosaccharide or the monosaccharide unit at the reducing end of the oligosaccharide is an aldose, wherein the stability of the one or more neutral mono- or oligosaccharides in the amorphous mixture is greater than the stability of an amorphous substance consisting of the one or more neutral mono- or oligosaccharides, and wherein the stability of the one or more neutral mono- or oligosaccharides in the amorphous mixture comprises reduced incidence of rearranged ulose from the one or more neutral mono- or oligosaccharides.

2. The method of claim 1, wherein the monosaccharide unit at the reducing end of the oligosaccharide is glucose.

3. The method of claim 2, wherein a galactose unit is attached to the glucose with a β1-4 interglycosidic linkage to form a lactose moiety.

4. The method of claim 3, wherein the oligosaccharide comprising the lactose moiety at the reducing end is a human milk oligosaccharide (HMO).

5. The method of claim 4, wherein the aqueous solution of the amorphous mixture comprising one or more HMOs and one or more acidic non-carbohydrate components comprises a concentration of the one or more HMOs is 5 w/w %.

6. The method of claim 5, wherein the HMO is selected from the group consisting of 2'-FL, DFL, 3-FL, an LNFP, LNnT and LNT; or a combination thereof.

7. The method of claim 5, wherein the aqueous solution comprises a pH of 4.2 to 5.8.

8. The method of claim 7, wherein the HMO in the aqueous solution is selected from the group consisting of 2'-FL, DFL, 3-FL, an LNFP, LNnT and LNT; or a combination thereof.

9. The method of claim 5, wherein the aqueous solution comprises a pH of 4.5 to 5.8.

10. The method of claim 9, wherein the HMO in the aqueous solution is selected from the group consisting of 3-FL, LNnT and LNT; or a combination thereof.

11. The method of claim 5, wherein the aqueous solution comprises a pH of 4.2-5.0.

12. The method of claim 11, wherein the HMO in the aqueous solution is selected from the group consisting of 2'-FL, LNFP-I, and LNnT; or a combination thereof.

13. The method of claim 1, wherein the one or more neutral mono- or oligosaccharidesis obtained from a bacterial fermentation prior to mixing the one or more acidic components and the one or more neutral mono- or oligosaccharides in an aqueous solution.

14. The method of claim 1, wherein the non-carbohydrate component comprises an inorganic acid.

15. The method of claim 14, wherein the inorganic acid is selected from the group consisting of sulfuric acid and its monosalts, HCl, HBr, and nitric acid or phosphoric acid and its mono- and disalts.

16. A method of preparing an amorphous mixture comprising one or more reducing neutral mono- or oligosaccharides and one or more acidic non-carbohydrate components, comprising mixing the one or more reducing neutral mono- or oligosaccharides with a sufficient amount of the one or more acidic components to reach a pH ranging from 3.5 to 5.8 in an aqueous solution, then spray-drying or freeze-drying the aqueous solution to obtain the amorphous mixture comprising the one or more reducing neutral mono- or oligosaccharides and the one or more acidic non-carbohydrate components, wherein the stability of the one or more reducing neutral mono- or oligosaccharides in the amorphous mixture is greater than the stability of an amorphous substance consisting of the one or more reducing neutral mono- or oligosaccharides, and wherein the stability of the one or more reducing neutral mono- or oligosaccharides in the amorphous mixture comprises reduced incidence of rearranged ulose from the one or more reducing neutral mono- or oligosaccharides.

17. The method of claim 16, comprising spray-drying the aqueous solution.

18. The method of claim 16, wherein the one or more reducing neutral mono- or oligosaccharides comprises at least one human milk oligosaccharide (HMO) with a lactose moiety at the reducing end of the HMO.

19. The method of claim 18, wherein the aqueous solution comprises a pH of 4.2-5.0.

* * * * *